US008028694B2

(12) United States Patent
Hickle

(10) Patent No.: US 8,028,694 B2
(45) Date of Patent: Oct. 4, 2011

(54) SYSTEMS AND METHODS FOR PROVIDING TREND ANALYSIS IN A SEDATION AND ANALGESIA SYSTEM

(75) Inventor: Randall S. Hickle, Lubbock, TX (US)

(73) Assignee: Scott Laboratories, Inc., Lubbock, TX (US)

(*) Notice: Subject to any disclaimer, the term of this patent is extended or adjusted under 35 U.S.C. 154(b) by 1366 days.

(21) Appl. No.: 10/677,482

(22) Filed: Oct. 3, 2003

(65) Prior Publication Data
US 2005/0039742 A1 Feb. 24, 2005

Related U.S. Application Data

(60) Provisional application No. 60/415,524, filed on Oct. 3, 2002.

(51) Int. Cl.
G08B 23/00 (2006.01)

(52) U.S. Cl. ............... 128/203.14; 128/203.12; 600/300

(58) Field of Classification Search ............. 128/200.24, 128/204.23, 204.21, DIG. 12, DIG. 13, 203.12, 128/203.14; 600/538, 500, 300, 301, 513, 600/523; 604/65, 49, 30–34, 50, 66.67, 118, 604/151, 246; 606/39, 42
See application file for complete search history.

(56) References Cited

U.S. PATENT DOCUMENTS

| 1,176,476 | A | 3/1916 | Jones |
| 2,185,068 | A | 12/1939 | Sholes et al. |
| 2,225,201 | A | 12/1940 | Anderson |
| 2,690,178 | A | 9/1954 | Bickford |
| 2,888,922 | A | 6/1959 | Bellville |
| 3,143,111 | A | 8/1964 | Green |
| 3,651,806 | A | 3/1972 | Hirshberg |
| 3,762,398 | A | 10/1973 | Schefke et al. |
| 3,898,983 | A | 8/1975 | Elam |
| 4,078,562 | A | 3/1978 | Friedman |
| 4,080,966 | A | 3/1978 | McNally et al. |
| 4,148,312 | A | 4/1979 | Bird |
| 4,275,727 | A | 6/1981 | Keeri-Szanto |
| 4,280,494 | A | 7/1981 | Cosgrove, Jr. et al. |
| 4,308,866 | A | 1/1982 | Jelliffe et al. |
| 4,392,849 | A | 7/1983 | Petre et al. |
| 4,533,346 | A | 8/1985 | Cosgrove, Jr. et al. |
| 4,550,726 | A | 11/1985 | McEwen |

(Continued)

FOREIGN PATENT DOCUMENTS
JP 04-309362 10/1992
(Continued)

OTHER PUBLICATIONS

International Search Report (EP) dated Apr. 9, 2004, corresponding to International Application No. PCT/US03/31906.

(Continued)

Primary Examiner — Steven O Douglas
(74) Attorney, Agent, or Firm — Hogan Lovells US LLP

(57) ABSTRACT

The present invention includes a sedation and analgesia system capable of gathering data from a single monitor associated with a single patient parameter in a manner that diminishes the probability of false positive alarms responses due to data artifact. The invention also includes a monitoring system that is able to detect imminent adverse patient conditions, where such conditions may be detected before an adverse patient condition actually occurs. The invention further includes methods for incorporating trend analysis into a sedation and analgesia system.

16 Claims, 3 Drawing Sheets

U.S. PATENT DOCUMENTS

| | | | | |
|---|---|---|---|---|
| 4,551,133 | A | 11/1985 | Zegers de Beyl et al. | 604/66 |
| 4,610,254 | A | 9/1986 | Morgan et al. | |
| 4,634,426 | A | 1/1987 | Kamen | |
| 4,681,121 | A | 7/1987 | Kobal | |
| 4,688,577 | A | 8/1987 | Bro | |
| 4,718,891 | A | 1/1988 | Lipps | |
| 4,731,051 | A | 3/1988 | Fischell | |
| 4,756,706 | A | 7/1988 | Kerns et al. | |
| 4,871,351 | A | 10/1989 | Feingold | |
| 4,942,544 | A | 7/1990 | McIntosh et al. | |
| 5,046,491 | A | 9/1991 | Derrick | |
| 5,065,315 | A | 11/1991 | Garcia | |
| 5,088,981 | A | 2/1992 | Howson et al. | |
| 5,094,235 | A | 3/1992 | Westenskow et al. | |
| 5,183,038 | A | 2/1993 | Hoffman et al. | |
| 5,231,981 | A | 8/1993 | Schreiber et al. | |
| 5,258,906 | A | 11/1993 | Kroll et al. | |
| 5,262,944 | A * | 11/1993 | Weisner et al. | 600/300 |
| 5,286,252 | A | 2/1994 | Tuttle et al. | |
| 5,309,908 | A | 5/1994 | Friedman et al. | |
| 5,352,195 | A | 10/1994 | McEwen | |
| 5,432,698 | A | 7/1995 | Fujita | |
| 5,438,983 | A | 8/1995 | Falcone | |
| 5,445,621 | A | 8/1995 | Poli et al. | |
| 5,507,277 | A | 4/1996 | Rubsamen et al. | 128/200.14 |
| 5,522,798 | A | 6/1996 | Johnson et al. | |
| 5,555,891 | A | 9/1996 | Eisenfeld | |
| 5,558,638 | A | 9/1996 | Evers et al. | |
| 5,614,887 | A | 3/1997 | Buchbinder | |
| 5,630,710 | A | 5/1997 | Tune et al. | |
| 5,653,739 | A | 8/1997 | Maurer et al. | |
| 5,676,133 | A | 10/1997 | Hickle et al. | |
| 5,677,290 | A | 10/1997 | Fukunaga | |
| 5,713,856 | A * | 2/1998 | Eggers et al. | 604/65 |
| 5,718,223 | A * | 2/1998 | Protas et al. | 128/204.21 |
| 5,724,025 | A | 3/1998 | Tavori | |
| 5,730,140 | A | 3/1998 | Fitch | |
| 5,733,259 | A | 3/1998 | Valcke et al. | |
| 5,795,301 | A * | 8/1998 | Yasukawa et al. | 600/500 |
| 5,795,327 | A | 8/1998 | Wilson | |
| 5,873,369 | A | 2/1999 | Laniado et al. | |
| 5,882,338 | A | 3/1999 | Gray | |
| 5,954,050 | A | 9/1999 | Christopher | |
| 5,957,885 | A | 9/1999 | Bollish et al. | |
| 5,980,501 | A | 11/1999 | Gray | |
| 6,024,089 | A * | 2/2000 | Wallace et al. | 128/204.21 |
| 6,062,216 | A | 5/2000 | Corn | |
| 6,099,481 | A | 8/2000 | Daniels et al. | |
| 6,148,814 | A | 11/2000 | Clemmer et al. | 128/200.24 |
| 6,152,130 | A | 11/2000 | Abrams et al. | |
| 6,158,430 | A | 12/2000 | Pfeiffer et al. | |
| 6,158,432 | A | 12/2000 | Biondi et al. | 128/204.21 |
| 6,165,151 | A | 12/2000 | Weiner | |
| 6,165,154 | A | 12/2000 | Gray et al. | |
| 6,182,667 | B1 | 2/2001 | Hanks et al. | |
| 6,186,977 | B1 | 2/2001 | Andrews et al. | |
| 6,289,238 | B1 | 9/2001 | Besson et al. | |
| 6,302,844 | B1 | 10/2001 | Walker et al. | |
| 6,305,372 | B1 | 10/2001 | Servidio | |
| 6,305,373 | B1 | 10/2001 | Wallace et al. | 128/204.21 |
| 6,328,708 | B1 | 12/2001 | Georgieff | 604/26 |
| 6,579,242 | B2 | 6/2003 | Bui et al. | |
| 6,629,933 | B1 | 10/2003 | Linder | |
| 6,757,558 | B2 * | 6/2004 | Lange et al. | 600/544 |
| 6,807,965 | B1 * | 10/2004 | Hickle | 128/204.23 |
| 7,081,095 | B2 * | 7/2006 | Lynn et al. | 600/538 |
| 7,089,927 | B2 * | 8/2006 | John et al. | 128/200.24 |
| 7,201,734 | B2 * | 4/2007 | Hickle | 604/67 |
| 2004/0111014 | A1 * | 6/2004 | Hickle | 600/300 |
| 2004/0129273 | A1 * | 7/2004 | Hickle | 128/207.14 |
| 2004/0133187 | A1 * | 7/2004 | Hickle | 604/890.1 |

FOREIGN PATENT DOCUMENTS

| | | |
|---|---|---|
| JP | 10-071137 | 3/1998 |
| JP | 10-248934 | 9/1998 |
| WO | 97/00092 | 1/1997 |
| WO | 97/07838 | 3/1997 |
| WO | 97/34648 | 9/1997 |
| WO | 98/10701 | 3/1998 |
| WO | 99/62403 | 12/1999 |
| WO | WO99/62403 | * 12/1999 |

OTHER PUBLICATIONS

Michel M. R. F. Struys, et al. "Comparison of Closed-loop Controlled Administration of Propofol Using Bispectral Index as the Controlled Variable versus 'Standard Practice' Controlled Administration," Anesthesiology, 95:6-17 (2001).

E. Mortier et al., "Closed-Loop Controlled Administration of Propofol Using Bispectral Analysis," Anaesthesia, 53:749-754 (1998).

J. B. Glen et al., "The Development of 'Diprifusor': A TCI System for Propofol," Anaesthesia, 53(1):13-21 (1998).

J.M. Gray et al., Development of the Technology for "Diprifusor" TCI Systems, Anaesthesia, 1988, 53, Supplement 1, pp. 22-27.

G.N.C. Kenny et al., "Closed-Loop Control of Propofol Anaesthesia," British Journal of Anaesthesia, 83(2): 223-228 (1999).

"A New Level of Control for Faster, More Predictable Recovery," BIS, Your Guide to the Hypnotic State During Anesthesia and Sedation.

P. Glass et al., "Intravenous Drug Delivery Systems," Anesthesia, pp. 389-416.

* cited by examiner

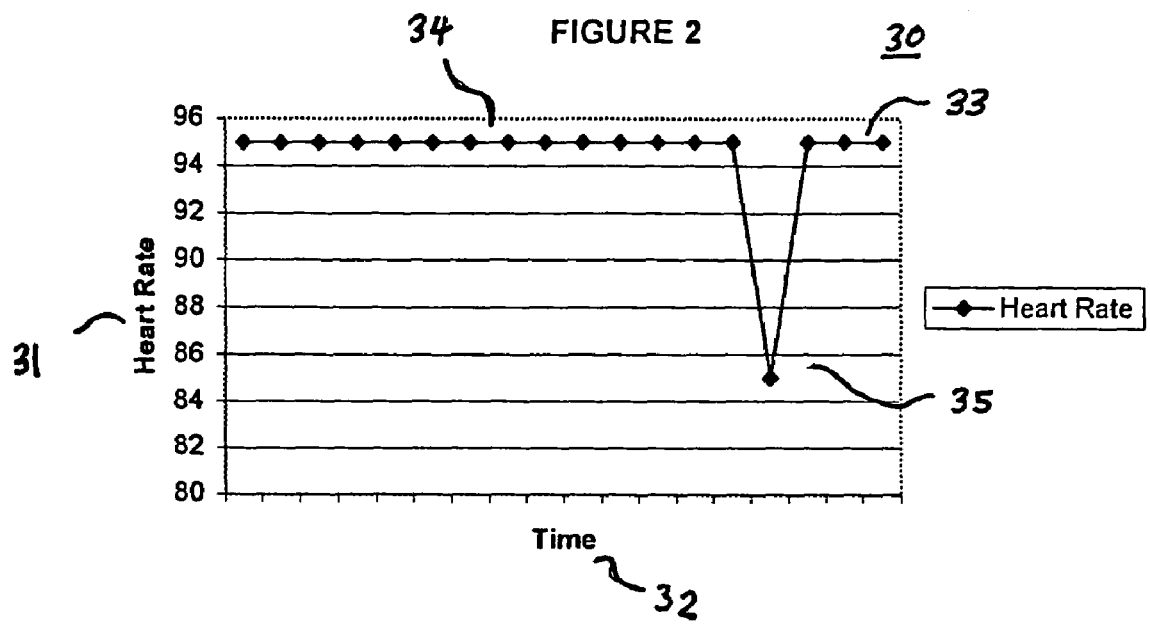
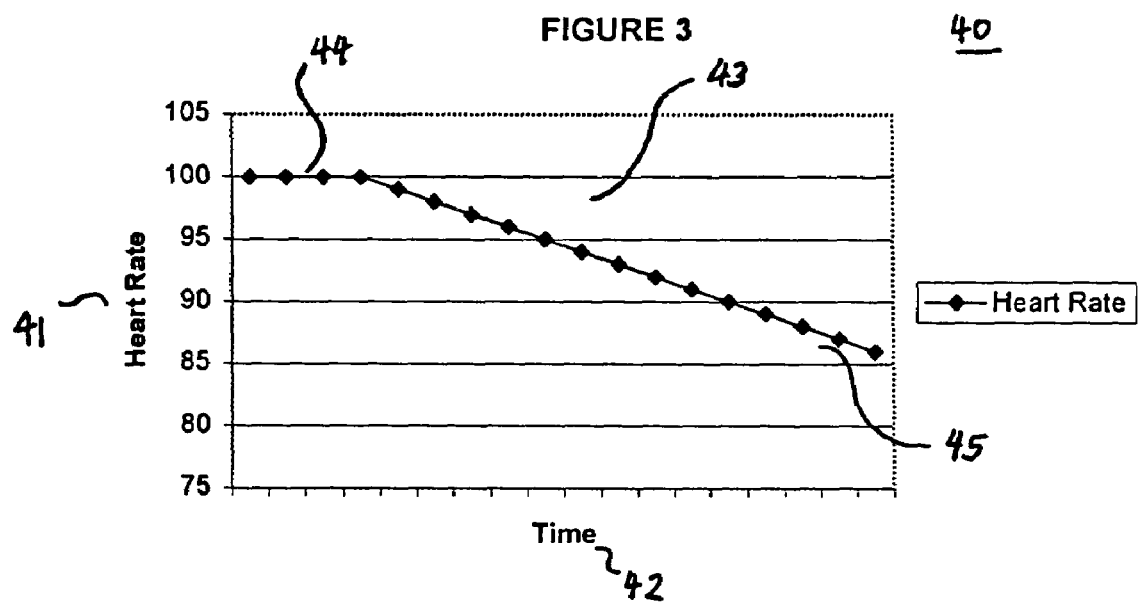

US 8,028,694 B2

SYSTEMS AND METHODS FOR PROVIDING TREND ANALYSIS IN A SEDATION AND ANALGESIA SYSTEM

CROSS REFERENCE TO RELATED APPLICATIONS

This application claims priority under 35 U.S.C. §119(e) to U.S. Provisional Patent Application No. 60/415,524, "Systems and Methods for Providing Trend Analysis in a Sedation and Analgesia System," filed Oct. 3, 2002, which is hereby incorporated by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates, in general, to trend analysis and, more particularly, to trend analysis incorporated into the monitoring, processing, and output features of a sedation and analgesia system.

2. Description of the Related Art

A sedation and analgesia system was developed to provide patients undergoing painful, uncomfortable or otherwise frightening (anxiety inspiring) medical or surgical procedures with a means for receiving sedative, analgesic, and/or amnestic drugs safely in a way that reduces the risk of overmedication with or without the presence of a licensed anesthesia provider. Due to significant advances in technology, the sedation and analgesia system is safe for use in hospital and ambulatory environments and may be operated by individuals other than trained anesthesiologists such as, for example, C.R.N.A.'s, trained physicians, or other trained operators. The sedation and analgesia system has gone far to meet the needs of practitioners who are unable to schedule anesthesia providers for every procedure where safe and effective sedation and analgesia could substantially mitigate fear and pain. The advent of a sedation and analgesia system devoted to these purposes provides these individuals with a drug delivery system integrated into a patient monitoring system that decreases the cognitive and manual workload required with the operation of anesthesia machines, yet keeps the clinician in the loop of patient management. The clinician maintains ultimate decision making responsibility following a "clinician knows best" philosophy. This advanced technology allows for a sedation and analgesia system to be operated at drug level effects less than general anesthesia without an anesthesia provider, providing the patient with a cost-effective and readily available means of sedation, amnesia, and/or analgesia.

An example of a sedation and analgesia system is described in U.S. patent application Ser. No. 09/324,759, filed Jun. 3, 1999 and incorporated herein by reference in its entirety. This sedation and analgesia system electronically integrates, for example, the delivery of one or more sedative, analgesic, and/or amnestic drugs, the delivery of positive airway pressure, decreases or increases in drug delivery, the delivery of oxygen, changes in drugs to, for example, an opioid antagonist, requests for additional information from patient monitors, and the triggering of alarms, with the electronic monitoring of one or more patient physiological conditions. In one form, the system of the '759 application uses one or more sets of stored data-defining parameters reflecting patient and system states, the parameters being accessed through software to conservatively manage and correlate drug delivery to safe, cost effective, optimized values related to the conscious patient's vital signs and other physiological conditions.

Spurious monitored data or other factors may cause the sedation and analgesia system to take potentially hazardous action, to fail to take action in critical situations, or to alarm unnecessarily. For example, the sedation and analgesia system may be monitoring a patient's heart rate with an electrocardiograph (ECG) when the ECG becomes erratic. Based on the single monitor, the sedation and analgesia system may signal an alarm indicating, for example, a dangerously low heart rate, when the erratic ECG data is actually spurious. A high frequency of false positive alarms may annoy clinicians and may result in less attention being given to truly life-threatening conditions.

Generally, monitoring systems incorporated into medical devices monitor a given patient parameter with a dedicated monitor. Safe data sets are then established for the monitored parameter, where if monitored data falls outside of the safe range, alarm responses are initiated. Such systems may provide high sensitivity, where most true adverse patient conditions are detected, however, such systems may also be prone to false positive alarms that result from data artifact that falls outside of the safe data set. Further, many patient parameters, such as heart rate, in the event of an impending adverse patient condition will drop in a linear or monotonic fashion towards thresholds of the safe data set indicating an adverse patient condition. In existing monitoring systems, such a drop is generally not detected until the data is outside the safe data set; however, it may be apparent from viewing a patient's heart rate over time that an adverse patient event is imminent several seconds before the patient parameter actually drops out of the safe data set. Waiting until data crosses established safe data set thresholds may leave clinicians to play catch up in situations where a patient is already experiencing an adverse condition.

SUMMARY OF THE INVENTION

The present invention includes a sedation and analgesia system capable of gathering data from a single monitor associated with a single patient parameter in a manner that diminishes the probability of false positive alarm responses due to data artifact. The invention also includes a monitoring system that is able to detect imminent adverse patient conditions, where such conditions may be detected before an adverse patient condition actually occurs.

The present invention also includes methods for incorporating trend analysis into a sedation and analgesia system. In one embodiment such a method comprises providing a patient monitor to monitor a single patient parameter and monitoring the patient with the monitor, so that data collected from the monitor is transmitted to a controller for the sedation and analgesia system. The method further comprises either inputting the trend into an algorithm of the sedation and analgesia system or analyzing the trend. Finally, the method further comprises initiating suitable action based on the trend analysis.

BRIEF DESCRIPTION OF THE DRAWINGS

FIG. 2 illustrates one example of a heart rate trend display according to the present invention;

FIG. 3 illustrates a further example of a heart rate trend display according to the present invention.

DETAILED DESCRIPTION OF THE INVENTION

Figure 1:
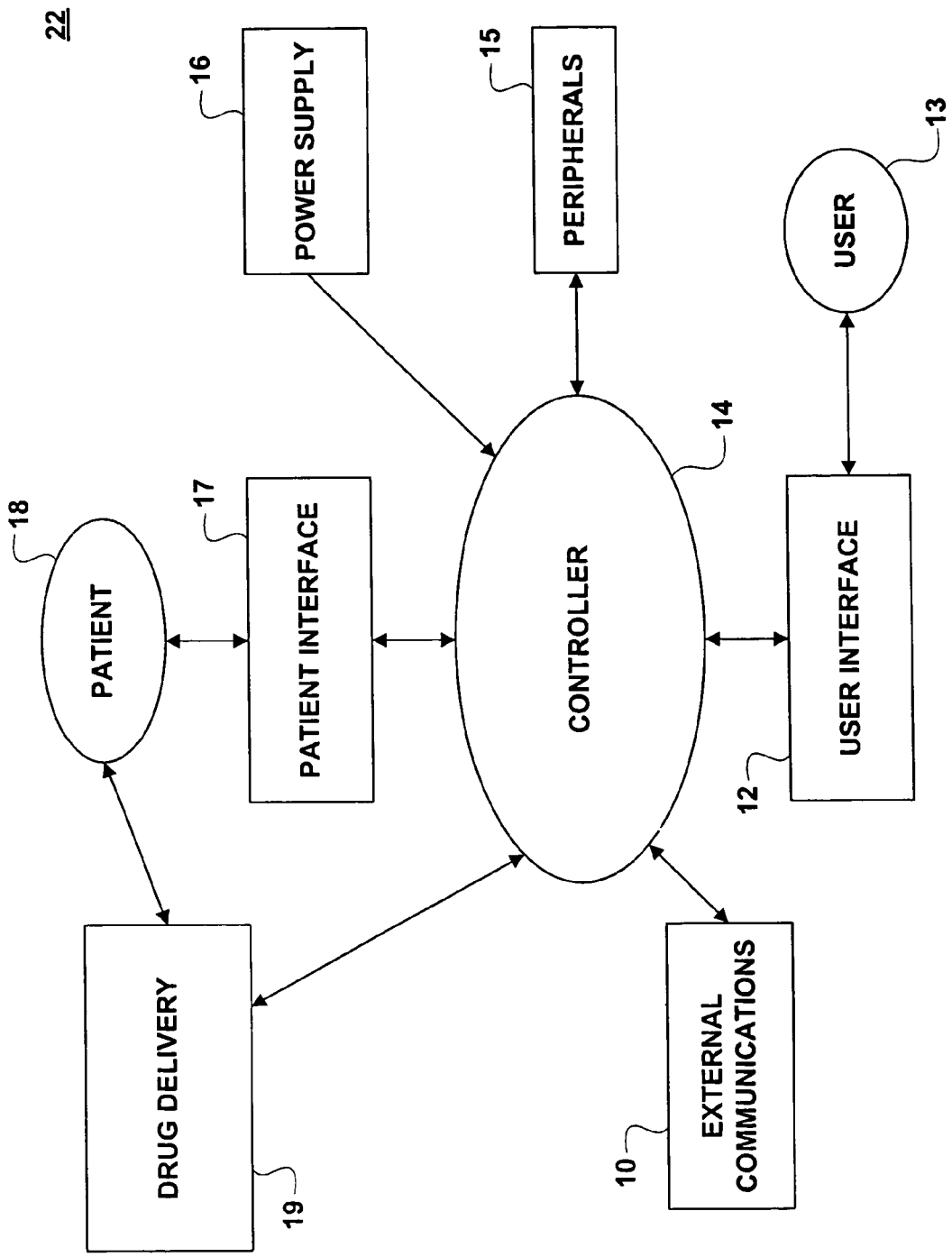
FIG. 1 illustrates a block diagram depicting one embodiment of a sedation and analgesia system in accordance with the present invention.

FIG. 1 illustrates a block diagram depicting one embodiment of a sedation and analgesia system 22 in accordance with the present invention having user interface 12, software controlled controller 14, peripherals 15, power supply 16, external communications 10, pressure delivery 11, patient interface 17, and drug delivery 19, where sedation and analgesia system 22 is operated by user 13 in order to provide sedation and/or analgesia to patient 18. An example of sedation and analgesia system 22 is disclosed and enabled by U.S. patent application Ser. No. 09/324,759, filed Jun. 3, 1999 and incorporated herein by reference in its entirety. Embodiments of user interface 12 are disclosed and enabled by U.S. patent application Ser. No. 10/285,689, filed Nov. 1, 2002 and incorporated herein by reference in its entirety.

Patient interface 17 includes one or more patient health monitors such as vital sign monitors and consciousness monitors including but not limited to non-invasive blood pressure monitors, pulse oximeters, capnometers, ECGs, patient consciousness assessment systems, ventilatory flow monitors, ventilatory pressure monitors, impedance plethysmogrophs (IPGs), gas analyzers, ventilatory temperature monitors, ventilatory humidity monitors, and acoustical monitors. The patient monitors of patient interface 17 may be electronically coupled to controller 14 and provide signals representing the patient's actual physiological condition. In one embodiment of the present invention, at least one monitor monitors a first patient parameter over time, where the trends of patient parameter are analyzed to determine whether adverse patient conditions are imminent and/or to ascertain whether data is likely due to artifact or representative of true patient condition. Monitored parameters may include, for example, heart rate, carbon dioxide levels, oxygen saturation, and blood pressure.

A patient's monitored parameter leaving a predetermined safe data set (e.g., heart rate dropping to a value that is considered too low) is generally preceded by a period of slow change, i.e., a trend, where that parameter eventually crosses the safe data set threshold (e.g., heart rate slowly dropping). Absent trend analysis, monitoring systems will generally only alert clinicians when a parameter falls outside of its safe data set, often leaving attending personnel scrambling to remedy an already potentially dangerous situation. The trend analysis provided by system 22 allows for pre-emptive warning to clinicians to a potentially dangerous situation that may be developing. Further, if a patient parameter falls outside of the safe data set due to data artifact, the trend analysis of the present invention may allow for sedation and analgesia system 22 to recognize the artifact due to a lack of preceding information indicative of an impending adverse patient condition. Controller 14 may compare the electronic feedback from patient interface 17 with data stored in a memory device over time, where such data may be evaluated as a trend of information rather than on a point-by-point basis.

Controller 14 may be programmed to control effectors (not shown) in response to the results of a trend analysis and/or stored data comparison. Effectors may be any suitable control feature capable of ensuring patient safety and clinician awareness. Effectors include, but are not limited to, drug decreases, drug increases, positive airway pressure changes, alarms, prealarms, oxygen delivery, triggers for additional data sampling from monitors, changes in drugs to, for example, carbon dioxide and opioid antagonists, and patient responsiveness queries. Effectors may occur silently without alerting the attending clinician; they may be signaled by user interface 12; and/or they may require confirmation from the user before being initiated.

FIG. 2 illustrates one embodiment of a display 30 depicting a heart rate trend 33 from a monitored patient. In the illustrated display, a safe heart range for the given patient and clinical context may be considered, for example, to be from 90-110 bpm. Trend 33 may be established based on heart rate y-axis 31 and time x-axis 32. Display 30 further illustrates period 34 in which the patient heart rate falls within the safe data set (at 95 bpm) and precludes alarming the clinician and/or taking steps to place the patient in a safe state. Following period 34, display 30 depicts period 35 of trend 33. Period 35, given the established safe data set, falls outside the predetermined safe range of acceptable heart rate. However, given the lack of supporting evidence that an adverse patient condition exists, where only a single data point falls below the 90 bpm threshold and there is no sloping drop towards the threshold consistent with most truly critical adverse patient conditions, it is likely that period 35 is the result of data artifact. Alarming the clinician during the illustrated example would likely result in a false positive alarm, thereby decreasing the specificity of the monitoring system and potentially annoying attending clinicians. Consistently initiating false positive alarms may result in clinicians becoming less attentive to alarms that may eventually be indicative of a truly adverse patient condition.

FIG. 3 illustrates a further example of a display 40 depicting heart rate trend 43 from a monitored patient. In the illustrated display, a safe heart range for the given patient and clinical context may be considered, for example, to be from 90-110 bpm. Trend 43 may be established based on heart rate y-axis 41 and time x-axis 42. Display 40 further illustrates period 44, where period 44 indicates that patient heart rate falls within the safe data set (at 100 bpm) and precludes alarming the clinician and/or taking steps to place the patient in a safe state. Following period 44, display 40 depicts period 45 of trend 43. Period 45 is a downwardly sloping portion of trend 43, where period 45 eventually crosses the established 90 bpm safe threshold. In the illustrated example, existing monitoring systems may only have alarmed when period 45 finally crossed the 90 bpm threshold, where such an imminent event may have been detectable earlier due to the morphology of the trend. As will be further discussed herein, by detecting slope variations in trend analysis, the present invention may be able to detect such imminent adverse patient conditions before they are full-blown, thereby allowing attending clinicians valuable time to ensure patient safety. Further, based on the slope of period 45, it is unlikely that such data indicative of a decaying patient condition results from spurious data. By incorporating trend analysis into sedation and analgesia system 22, the present invention may be able to increase the specificity of patient monitoring by reducing the effects of data artifact while catching truly critical patient events earlier by evaluating trends of monitored patient parameters.

Figure 4:
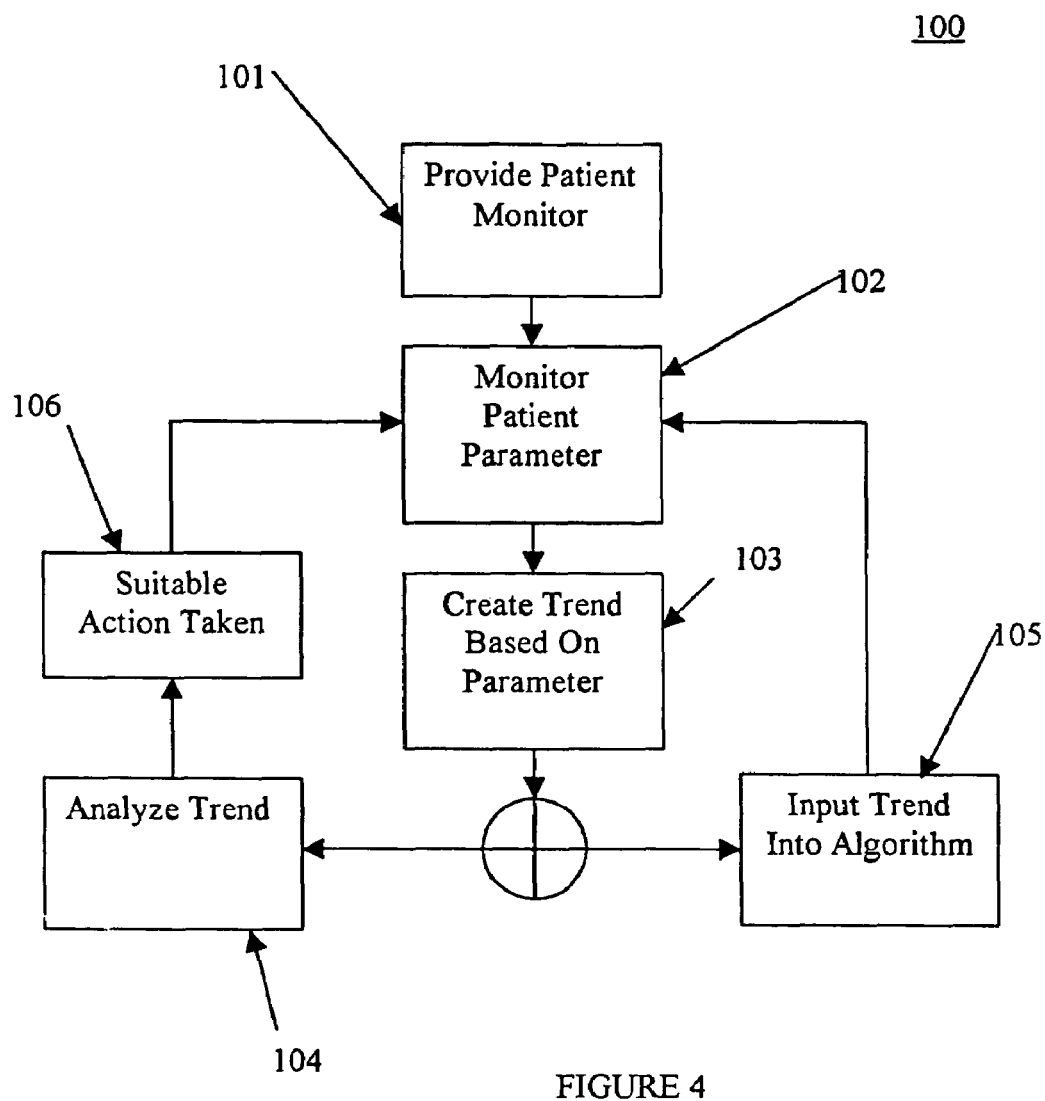
FIG. 4 shows one embodiment of a method for incorporating trend analysis into a sedation and analgesia system according to the present invention.

FIG. 4 illustrates one embodiment of a method 100 for incorporating trend analysis into a sedation and analgesia system 22. Method 100 comprises step 101, which includes providing a patient monitor to monitor a given patient parameter. The monitor of step 101 may be, for example, a pulse oximeter to measure heart rate, however, any suitable monitor of any suitable patient parameter is in accordance with the present invention. Step 102 comprises monitoring the patient with the monitor of step 101, where data collected from the monitor may be transmitted to controller 14 of sedation and analgesia system 22 (FIG. 1).

Step 103 comprises creating a trend based on data received from the monitor of step 101. For example, FIGS. 2 and 3 illustrate trends created by connecting data points over time. Such trends may be established by any suitable means, where such trends may further be displayed for visual analysis by an attending clinician. Following step 103, method 100 may proceed to step 104 and/or step 105.

Step 104 comprises analyzing the trend established in accordance with step 103. For example, such trends may be analyzed in the following ways: (1) if the trend has a linear, quasi-linear or monotonic nature, the slope of the trend may be calculated to determine whether the trend is progressing inexorably towards the outer limits of the safe data set; (2) if the trend does not tend to follow a single (e.g., linear) path, multiple slopes for trend variation may be calculated to ascertain where the trend appears to be headed; (3) if the trend is polynomial in nature, coefficients of the polynomials may be calculated to ascertain the direction of the trend; and (4) using a least mean squares error technique and other such algorithms to curve fit the trend and predict if and when it will step beyond the safe data set. From such analyses, the present invention comprises monitoring the trend of any suitable patient parameter in a fashion that indicates the most accurate depiction of true patient condition.

In accordance with step 104, based on the above analyses, method 100 may then evaluate the monitored trends against established safe data sets. Referring to FIG. 3 for example, if the slope of period 45 exceeded a particular rate, where such a slope is indicative of an imminent adverse patient condition, sedation and analgesia system 22 may initiate a pre-alarm or other suitable action, as will be further discussed herein. Step 104 further comprises calculating a probability value, by means commonly known in the art, for whether data presented to controller 14 is actually indicative of a slope change. Based on comparative analysis, if such data is reflective of a slope change, sedation and analgesia system 22 may then evaluate such data to determine whether the slope indicates an imminent adverse patient condition. Further, with reference to FIG. 2, such an analysis may result in the dismissal of period 35 as data artifact, thereby reducing the probability that sedation and analgesia system 22 will initiate false positive alarms. Even the incorporation of trend analysis into a single monitored patient parameter may help increase the specificity of sedation and analgesia system 22 (by decreasing the effects of data artifact) and help catch instances of adverse patient conditions before they become pronounced. Such trend analysis may also be applied to multiple parameters for sedation and analgesia system 22 with further advantageous results.

Step 105 comprises inputting the trend created in step 103 into any suitable algorithm of sedation and analgesia system 22. Such a trend may be combined with multiple other trends from related patient parameters to further decrease the effects of data artifact and to clarify inconclusive data by the incorporation of such sensor fusion. Further, such trends may be incorporated as a feature of orthogonal redundancy, where orthogonal redundancy refers to monitoring a single patient parameter with multiple monitors simultaneously. Sensor fusion is further described in commonly assigned and co-pending U.S. application Ser. No. 10/677,481 entitled "Systems and Methods for Providing Sensor Fusion," filed on Oct. 3, 2003, which is herein incorporated by reference. Orthogonally redundant monitoring is further described in commonly assigned and co-pending U.S. application Ser. No. 10/677,483 entitled "Methods and Systems for Providing Orthogonally Redundant Monitoring in a Sedation and Analgesia System," filed on Oct. 3, 2003, which is herein incorporated by reference. Incorporating trend analysis into such redundancy may further increase the specificity and sensitivity of sedation and analgesia system 22 by decreasing the probability of initiating both false negative and false positive alarm states. Such trends may also be integrated into neural networks, where neural networks are systems of computerized intelligence capable of picking out complex patterns and arriving at correct decisions even if presented with an incomplete or ambiguous picture.

The present invention comprises the incorporation of trend analysis into sedation and analgesia system 22, where such an integration may allow controller 14 to more accurately analyze data with respect to patient condition. By monitoring a given parameter, it may be possible to diminish the presence of artifact and to anticipate imminent adverse patient events, however the use of a trend in cooperation with trends monitoring a single parameter, trends monitoring multiple related parameters, and neural networks further increases the ability of sedation and analgesia system 22 to take actions based on a true picture of patient condition. Those actions taken based on algorithms associated with sedation and analgesia system 22 in accordance with step 105 include those illustrated in step 106 as well as any other suitable action helpful in ensuring patient safety.

Step 106 comprises taking suitable action based on the trend analysis of step 104. If, for example, from trend analysis it is determined that data outside of a safe data set is due to artifact (such as in FIG. 2), method 100 may proceed to step 102 and sedation and analgesia system 22 may take no other action. Maintaining normal function in the presence of data artifact may decrease the probability of false positive alarms and may allow sedation and analgesia to monitor more directly actual patient condition. If upon trend analysis it is determined that an adverse patient episode is imminent (such as in FIG. 3), step 106 comprises initiating a pre-alarm. A pre-alarm may be any suitable action taken to alert the attending clinician of a high probability of an impending adverse patient condition. Such pre-alarms may signal visually and/or audibly, and may include, for example, decreasing drug levels; changing drugs to, for example, carbon dioxide and/or an opioid antagonist; triggering a request for gathering more information from patient monitors; delivering oxygen; testing patient responsiveness; and delivering positive airway pressure. Such actions may also be taken if the patient exceeds the established safe thresholds, where alarms for such events may, for example, be more emphatic than those associated with pre-alarms. By taking action early based on trend analysis, sedation and analgesia system 22 may alert clinicians early and potentially obviate many adverse patient conditions all together. For example, if a trend representative of heart rate indicates that heart rate is dropping precipitously and is not due to artifact, sedation and analgesia system 22 may pause drug delivery before the patient's heart rate falls outside the established safe data set. Such a proactive action may obviate or reduce the severity of adverse patient conditions.

While exemplary embodiments of the invention have been shown and described herein, it will be obvious to those skilled in the art that such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope by the claims as they will be allowed.

The invention claimed is:

1. A sedation and analgesia system, comprising:
at least one patient health monitor device adapted so as to be coupled to a patient and so as to measure a patient parameter reflecting a physiological condition of the patient;
a user interface;
a drug delivery controller supplying one or more drugs to the patient; and
an electronic controller interconnected with the patient health monitor, the user interface, and the drug delivery controller, said electronic controller having a data set reflecting parameters of at least one monitored patient physiological condition, wherein said electronic controller receives said patient parameter and, throughout operation of the sedation and analgesia system, continually analyzes trends of said patient parameter in accord with the data set to determine whether adverse patient conditions are imminent and to initiate suitable action.

2. The sedation and analgesia system of claim 1, further comprising one or more effectors for ensuring patient safety and clinician awareness, wherein said electronic controller is interconnected with the effector and controls the effector in accordance said trends of said patient parameter.

3. The sedation and analgesia system of claim 1, wherein said electronic controller provides preemptive warnings in response to adverse trends of said patient parameter within a range of said data set.

4. The sedation and analgesia system of claim 1, wherein said electronic controller evaluates said patient parameter measurements against said trends.

5. The sedation and analgesia system of claim 1, wherein said patient parameter is one derived from capnometry, pulse oximetry, and blood pressure.

6. The sedation and analgesia system of claim 1, wherein said patient parameter is heart rate.

7. The sedation and analgesia system of claim 1, wherein said at least one patient health monitor is one of an electrocardiograph and a pulse oximeter.

8. A method for incorporating trend analysis into a sedation and analgesia system, comprising the steps of:
providing a patient monitor for a patient to monitor a single patient parameter;
monitoring the patient with the monitor, wherein data collected from the monitor may be transmitted to a controller of the sedation and analgesia system;
creating a trend based on the data received from the monitor;
at least one of inputting the trend into an algorithm of the sedation and analgesia system and, throughout operation of the sedation and analgesia system, continually analyzing the trend to determine whether adverse patient conditions are imminent; and
initiating suitable action based on the trend analysis.

9. The method of claim 8, wherein said step of analyzing includes at least one of calculating the slope of the trend, calculating multiple slopes for trend variation, calculating coefficients of polynomials of the trend, and curve-fitting the slope using a least mean square error technique.

10. The method of claim 8, further comprising the step of calculating a probability value for whether data presented to the controller is actually indicative of a slope change.

11. The method of claim 8, wherein the trend is analyzed in combination with trends from related patient parameters.

12. The method of claim 9, wherein the trend is incorporated as a feature of orthogonal redundancy.

13. The method of claim 8, wherein the trend is integrated into at least one neural network.

14. The method of claim 8, wherein the suitable action comprises at least one of continuing to monitor, initiating a pre-alarm, pausing drug delivery, and initiating a full alarm.

15. The system of claim 2, wherein said effector is one or more of a drug decrease, drug increase, positive airway pressure change, pre-alarm, oxygen delivery, trigger for additional data sampling from monitors, change in drugs, and patient responsiveness query.

16. The system of claim 1, wherein the suitable action comprises at least one of initiating a pre-alarm, pausing drug delivery, and initiating a full alarm.

* * * * *